US00PP28972P2

(12) United States Plant Patent
Harrell

(10) Patent No.: US PP28,972 P2
(45) Date of Patent: Feb. 20, 2018

(54) ***RHODODENDRON* PLANT NAMED 'WHA01'**

(50) Latin Name: *Rhododendron hybrida*
Varietal Denomination: WHA01

(71) Applicant: Winfred Harrell, Plant City, FL (US)

(72) Inventor: Winfred Harrell, Plant City, FL (US)

( * ) Notice: Subject to any disclaimer, the term of this patent is extended or adjusted under 35 U.S.C. 154(b) by 0 days.

(21) Appl. No.: 15/330,181

(22) Filed: Aug. 18, 2016

(51) Int. Cl.
*A01H 5/02* (2006.01)

(52) U.S. Cl.
USPC ..... Plt./239

(58) Field of Classification Search
USPC ..... Plt./239
See application file for complete search history.

*Primary Examiner* — Anne M Grunberg
(74) *Attorney, Agent, or Firm* — Cassandra Bright

(57) ABSTRACT

A new and distinct *Rhododendron* cultivar named 'WHA01' is disclosed, characterized by distinctive full double pink flowers. Plants are upright and vigorous. Plants bloom Spring, Summer and Fall and exhibit good tolerance to environmental stressors. The new cultivar is a *Rhododendron*, suitable for ornamental garden purposes.

2 Drawing Sheets

Figure 1:
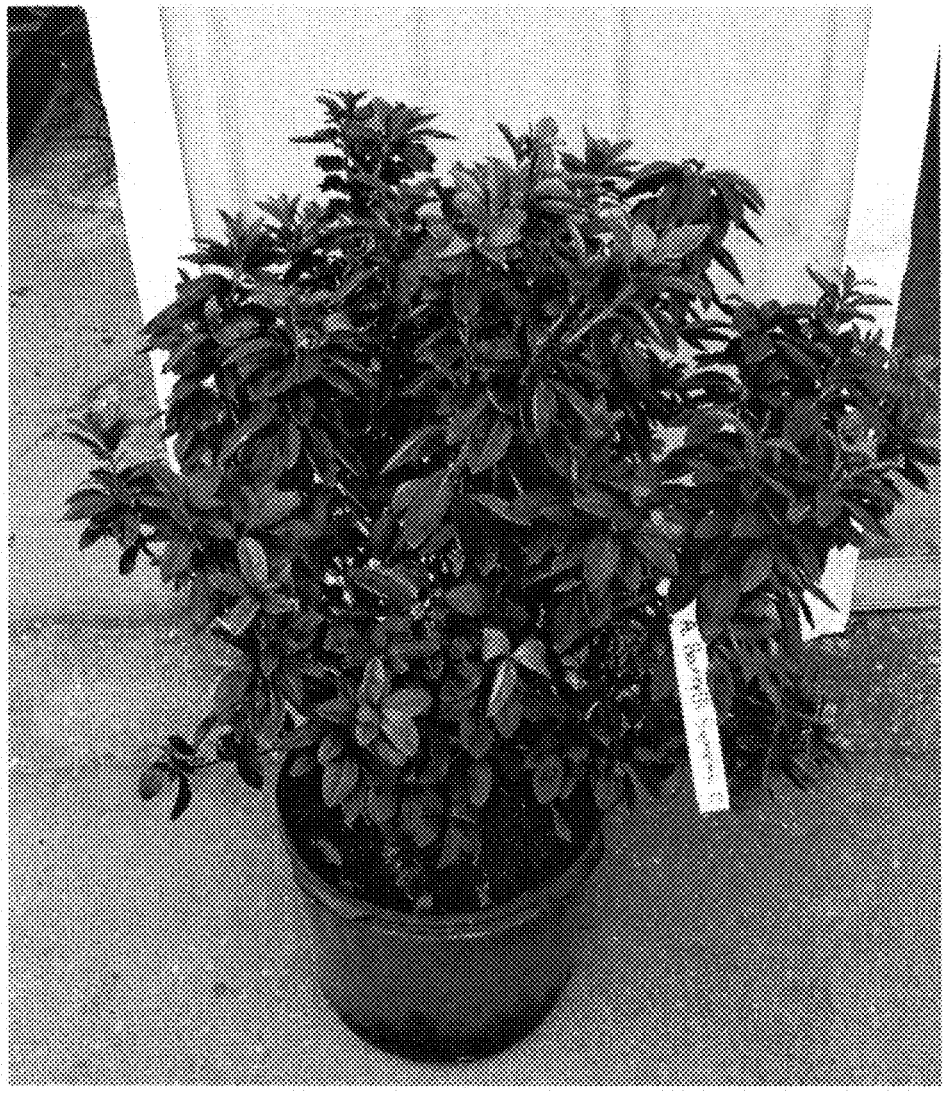

Latin name of the genus and species: *Rhododendron hybrida.*

Variety denomination: 'WHA01'.

BACKGROUND OF THE INVENTION

The new cultivar is a product of chance discovery by the inventor, Winfred Harrell. This new variety, hereinafter referred to as 'WHA01', was discovered as a single branch, naturally occurring mutation of *Rhododendron* 'White Ruffle' unpatented. The new variety was selected by the inventor during 2012 at a commercial nursery in Plant City, Fla.

After identifying the new variety as a potentially interesting selection, the inventor first propagated the new variety by softwood cuttings at the same commercial nursery in Plant City, Fla. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'WHA01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WHA01' These characteristics in combination distinguish 'WHA01' as a new and distinct *Rhododendron* cultivar:

1. Unique Spring, Summer, and Fall blooming, plants re-blooming throughout these seasons.
2. Fully double flowers, with many interior petals.
3. Self-Cleaning flowers
4. Strong plant, tolerant of a variety of environmental stressors.
5. Plants very well suited for landscape use, including hedge planting or as a specimen.

7. Observed hardy to Zone 7 and potentially Zone 6.
8. Large foliage.
9. Bright pink flower color.

COMPARISON TO PARENT VARIETY

'WHA01' is similar in most horticultural characteristics to the parent *Rhododendron hybrida* 'White Ruffle'. Plants of the new cultivar 'WHA01' however differ in the following:

1. The new variety has a red-purple flower, the parent has a white flower.

COMMERCIAL COMPARISON

'WHA01' can be compared to the commercial variety *Rhododendron hybrida* 'RLH1-2P8' U.S. Plant Pat. No. 21,477. Plants of the new cultivar 'WHA01' are similar to plants of 'RLH1-2P8' in most horticultural characteristics, however, plants of the new cultivar 'WHA01' differ in the following:

1. Plants of the new variety grow taller than plants of this comparator.
2. Plants of 'WHA01' grow more vigorously than plants of this comparator.
3. Foliage of 'WHA01' is larger than foliage of this comparator.
4. Plants of the new variety have a more upright form, compared to the globose form of this comparator.

'WHA01' can be compared to the commercial variety *Rhododendron hybrida* 'Roblec' U.S. Plant Pat. No. 15,339. Plants of the new cultivar 'WHA01' are similar to plants of 'Roblec' in most horticultural characteristics, however, plants of the new cultivar 'WHA01' differ in the following:

1. 'WHA01' has flowers colored near Red-Purple 57D; flowers of 'Roblec' are colored near Red-Purple 73B.
2. Plants of 'WHA01' grow more vigorously than plants of 'Roblec'.
3. Foliage of 'WHA01' is larger than foliage of 'Roblec'.
4. Plants of 'WHA01' are more upright in habit than plants of 'Roblec'

BRIEF DESCRIPTION OF THE PHOTOGRAPHS

The accompanying photograph in FIG. 1 illustrates in full color a 2 year old plant of the new variety in a 5 gallon pot.

Figure 2:
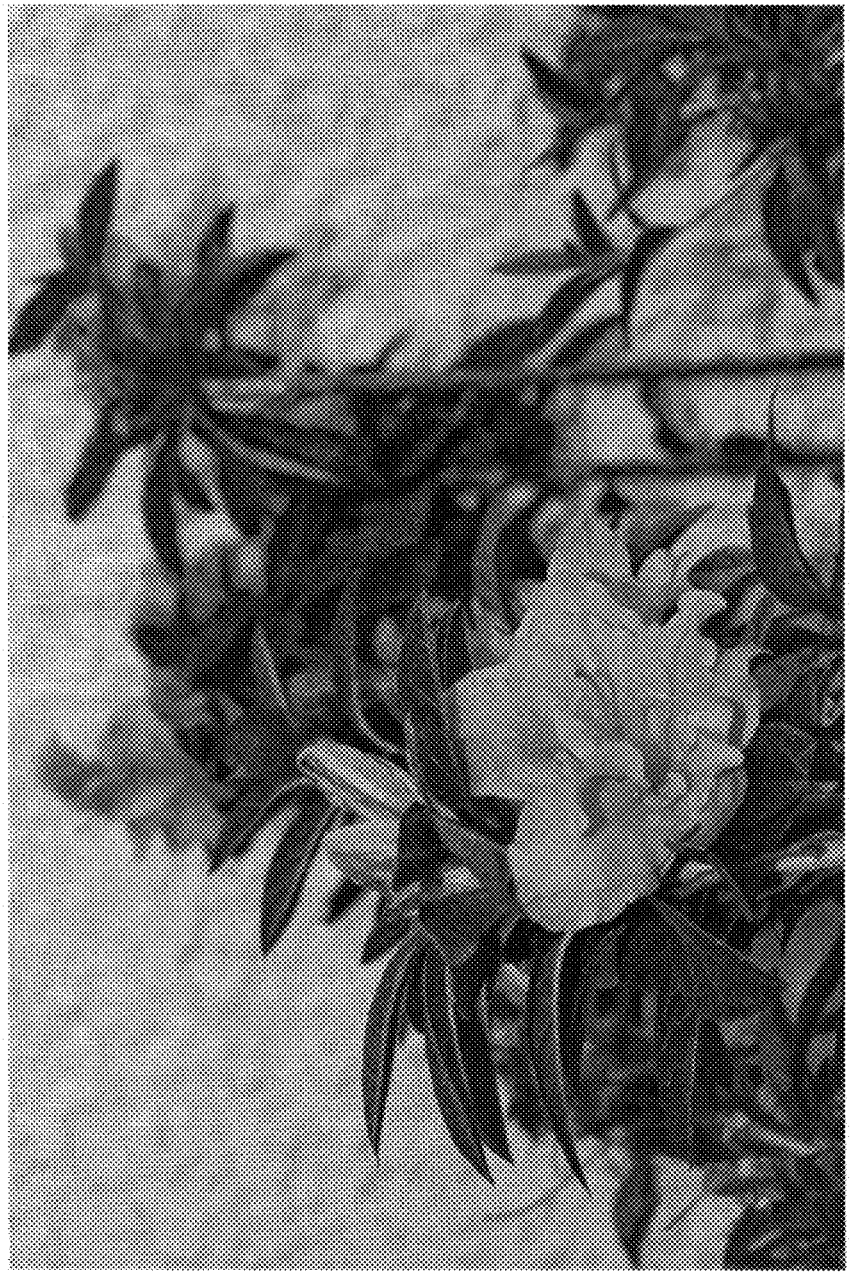

FIG. 2 illustrates in full color a close up of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'WHA01' plants grown outdoors in Loxley, Ala. Plants are approximately 2 years old, in a 3 gallon nursery container. Measurements and numerical values represent averages of typical plant types.

Botanical classification: *Rhododendron hybrida* 'WHA01'.

PROPAGATION

Typically by semi-hardwood cuttings in Spring and Summer.

Root description: Fine, fibrous young roots, well branched. Colored near RHS Grey-Brown 199A.

PLANT

Growth habit: Upright evergreen shrub.

Height: Approximately 75 cm to top of foliar and flowering plane.

Plant spread: Approximately 85 cm.

Branching characteristics: Well branched, approximately 3 to 6 primary branches from the center of the plant. Branches occur at approximately 15° to 45° angles. Each primary branch has 4 to 8 lateral branches.

Primary branches:

- *Length of primary branches*.—Average range 15 to 30 cm.
- *Diameter of primary branches*.—Approximately 1.01 cm.
- *Primary branch strength*.—Very strong, difficult to break.
- *Primary branch color*.—Near Greyed-Orange 177A, streaked Greyed-Green 197B.
- *Primary branch texture*.—Scaly, rough.

Lateral branches:

- *Number of lateral branches*.—Approximately 4 to 8 per primary branch.
- *Length of lateral branches*.—Average range 12 to 30 cm.
- *Diameter of lateral branches*.—Average 0.4 to 0.7 cm.
- *Lateral branch strength*.—Very strong, flexible.
- *Lateral branch color*.—New growth near RHS Yellow-Green 144B; oldest branches become woody, colored near Greyed-Orange 177A.
- *Lateral branch texture*.—Immature growth hirsute. Older growth scaly, hirsute.

Internode length: Average range 2.5 to 4.0 cm.

Age of plant described: Approximately 2 years.

FOLIAGE

Leaf:

- *Type*.—Simple.
- *Arrangement*.—Sub-opposite.
- *Average length*.—Average range 4.2 to 6.8 cm.
- *Average width*.—Average range 2.2 to 2.7 cm.
- *Shape of blade*.—Obovate.
- *Apex*.—Mucronate.
- *Base*.—Broad attenuate.
- *Attachment*.—Stalked.
- *Margin*.—Entire. Cilliate.
- *Texture of top surface*.—Sparsely pubescent. Hairs appressed.
- *Texture of bottom surface*.—Sparsely pubescent. Denser and longer hairs present along main vein and margin.
- *Color*.—Young foliage upper side: Near RHS Green 137A. Young foliage under side: Near RHS Green 138A. Mature foliage upper side: Near RHS Green 139A. Mature foliage under side: Near RHS Green 137C.

Venation:

- *Type*.—Pinnate.
- *Venation color upper side*.—Near RHS Yellow-Green N144A.
- *Venation color under side*.—Near RHS Yellow-Green 144C.

Petiole:

- *Length*.—About 0.5 cm.
- *Diameter*.—About 0.2 cm.
- *Color*.—Upper Surface: Near RHS Yellow-Green 144C. Lower Surface: Near RHS Yellow-Green N144B.

FLOWER

Bloom period: Plants begin flowering in the Spring, and continue to produce flowers throughout Summer and Fall in the Southern United States.

Flower:

- *Arrangement*.—Axillary clusters of perfect, double funnel shaped individual flowers. Typically 3 to 5 flowers per cluster.

Inflorescence:

- *Height*.—Average 9.0 cm.
- *Diameter*.—Average 10.0 cm.

Peduncle: Not present, inflorescence pedicels emerge directly from node.

Pedicel:

- *Length*.—Average 0.7 cm to 1.7 cm.
- *Diameter*.—0.4 cm.
- *Color*.—Near RHS Yellow-Green 145A.
- *Texture*.—Densely pubescent. Long, soft hairs colored near Greyed-Red 180D.
- *Aspect*.—Straight. Angle of attachment, approximately 45° angle from stem.
- *Strength*.—Very sturdy and flexible.

Flowers:

- *Length*.—Average 3.9 cm.
- *Diameter*.—Average 8.0 cm.
- *Facing direction*.—Outwardly and upwardly facing.
- *Persistent or self-cleaning*.—Self-cleaning.
- *Fragrance*.—Faint sweet smell.

Tube:

- *Tube length*.—Approximately 1.0 cm.
- *Tube width a widest point*.—Approximately 1.0 cm.
- *Tube width and narrowest point*.—Approximately 0.8 cm.

Petals:

*Unfused petal segments*.—Length: Approximately 3.5 cm. Width: Approximately 2.8 cm.

*Apex*.—Typically acute. Outermost ring of petals can be mucronate.

*Shape of petal*.—Unfused portion, obovate.

*Petal margin*.—Entire, ruffled.

*Petal arrangement*.—Overlapping, bilateral symmetry dissecting bottom petal. Petals fused approximately ¼ distance from base.

*Petal number*.—Average 15 to 20 full petals. 5 to 10 irregularly shaped and sized petaloids mainly in center of flower.

*Petal texture*.—Smooth, ridged.

*Petal appearance*.—Slightly shiny/irredescent.

*Color*.—Upper surface at first opening: Near RHS Red-Purple N57D, basal dots near 63A. Very fine margin coloration near 63A. Under surface at first opening: Near RHS Red-Purple N57D, faint streaks near 63A. Very fine margin coloration near 63A. Inner surface at maturity: Near RHS Red-Purple N57D, basal dots near 63A. Very fine margin coloration near 63A. Outer surface at maturity: Near RHS Red-Purple N57D, faint streaks near 63A. Very fine margin coloration near 63A. Upper surface at fading: Near RHS Red-Purple N57D, faint streaks near 63C. Very fine margin coloration near 63A. Under surface at fading: Near RHS Red-Purple N57D, faint streaks near 63D. Very fine margin coloration near 63A.

Bud:

*Shape*.—Elliptic.

*Length*.—2.9 cm.

*Diameter*.—1.7 cm.

*Color*.—Near RHS Red-Purple N57D.

Calyx/sepals: Sepals self-cleaning before flower is fully open.

*Quantity per flower*.—5 sepals.

*Shape*.—Narrow deltate.

*Length*.—2.0 cm.

*Width*.—1.0 cm.

*Apex*.—Acute.

*Base*.—Fused.

*Margin*.—Entire.

*Texture*.—Exterior surface pubescent, interior surface glabrous.

*Color*.—Interior Surface: Near RHS Yellow-Green 151D, base flushed near Red 53A. Apex Green 137A. Outer Surface: Near RHS Yellow-Green 151C, base and significant streaks throughout colored near Greyed-Purple 187B.

REPRODUCTIVE ORGANS

Stamens:

*Number*.—1 or 2 full stamens, 1 or 2 undeveloped stamenoidal structures present.

*Stamen length*.—1.5 cm.

*Width*.—0.1 cm.

*Color*.—Near RHS Red-Purple 62A.

*Anthers*.—Length: Approximately 0.2 cm. Color: Near RHS Red-Purple 72A. Pollen: Not observed.

Pistil:

*Number*.—1.

*Length*.—Average 4.4 cm.

*Style*.—Length: Average 3.4 cm. Color: Near RHS Red-Purple N57C.

*Stigma*.—Globular, colored near Red-Purple N66A.

*Ovary*.—Sericeous texture. Approximately 0.3 cm in diameter, 1.0 cm long. Colored near Red 55D.

OTHER CHARACTERISTICS

Disease and pest resistance: Not observed to be susceptible nor resistant to normal diseases and pests of *Rhododendron*.

Temperature tolerance: Observed hardy to USDA Zone 7, potentially hardy to zone 6.

Fruit/seed production: Not observed to date.

What is claimed is:

1. A new and distinct cultivar of *Rhododendron* plant named 'WHA01' as herein illustrated and described.

* * * * *